(12) United States Patent
Lee et al.

(10) Patent No.: US 10,081,017 B2
(45) Date of Patent: Sep. 25, 2018

(54) METHOD AND SYSTEM FOR ULTRA-HIGH DYNAMIC RANGE NUCLEIC ACID QUANTIFICATION

(71) Applicant: THE REGENTS OF THE UNIVERSITY OF CALIFORNIA, Oakland, CA (US)

(72) Inventors: Abraham P. Lee, Irvine, CA (US); Andrew C. Hatch, Irvine, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 221 days.

(21) Appl. No.: 14/878,636

(22) Filed: Oct. 8, 2015

(65) Prior Publication Data
US 2016/0101418 A1 Apr. 14, 2016

Related U.S. Application Data

(60) Provisional application No. 62/061,646, filed on Oct. 8, 2014.

(51) Int. Cl.
| | |
|---|---|
| *C12Q 1/68* | (2018.01) |
| *C12P 19/34* | (2006.01) |
| *B01L 7/00* | (2006.01) |
| *C12Q 1/6825* | (2018.01) |
| *C12Q 1/6851* | (2018.01) |
| *B01L 3/02* | (2006.01) |
| *B01L 3/00* | (2006.01) |

(52) U.S. Cl.
CPC ............ *B01L 7/52* (2013.01); *B01L 3/0241* (2013.01); *B01L 3/502784* (2013.01); *C12Q 1/6825* (2013.01); *C12Q 1/6851* (2013.01); *B01L 2300/0864* (2013.01)

(58) Field of Classification Search
None
See application file for complete search history.

(56) References Cited

U.S. PATENT DOCUMENTS

| | | | | |
|---|---|---|---|---|
| 2010/0092973 | A1* | 4/2010 | Davies | ............ B01L 3/502784 |
| | | | | 435/6.19 |
| 2012/0164652 | A1* | 6/2012 | Clemens | ............ G01N 21/6428 |
| | | | | 435/6.12 |

OTHER PUBLICATIONS

Hatch, Andrew C. et al., 1-Million droplet array with wide-field fluorescence imaging for digital PCR, Lab Chip, 2011, 11, 3838-3845.
Sahoo, P.K. et al., Comput. Vision Graphics Image Process., 1988, 41, 233-260.
Hatch, Andrew Carter, High Throughput Digital Microfluidics for On-Chip Nucleic Acid Detection, Dissertation, submitted in partial satisfaction of the requirements for the degree of Docto of Philosophy in Biomedical Engineering, 2011, (176pages).

* cited by examiner

*Primary Examiner* — Young J Kim
(74) *Attorney, Agent, or Firm* — Vista IP Law Group LLP

(57) ABSTRACT

A method of quantifying nucleic acids in a sample includes generating a plurality of droplets in oil within a microfluidic device, wherein at least some of the droplets comprise a nucleic acid, amplification reagents, and a fluorescent probe or dyes contained therein. The droplets are delivered to a collection chamber to form an array of droplets. The droplets are subject to thermal cycling within the collection chamber a plurality of times to perform nucleic acid amplification within the droplets. The array of droplets is imaged during the plurality of thermal cycles as well as at a thermal cycle endpoint. An initial concentration of nucleic acid in the sample is calculated based on at least one of: a ratio of aqueous phase droplets exhibiting fluorescence within the array at the thermal cycle endpoint or a cycle threshold (Ct) of one or more aqueous phase droplets within the array.

11 Claims, 7 Drawing Sheets

Pour PDMS Over SU-8 Master Mold

Insert Spacers and Glass Slide

Cure PDMS in 60 °C Oven

(View Rotated 90°)

Release from Mold and Core Holes

Plasma Bond to Glass Slide

METHOD AND SYSTEM FOR ULTRA-HIGH DYNAMIC RANGE NUCLEIC ACID QUANTIFICATION

RELATED APPLICATION

This Application claims priority to U.S. Provisional Patent Application No. 62/061,646 filed on Oct. 8, 2014, which is hereby incorporated by reference in its entirety. Priority is claimed pursuant to 35 U.S.C. § 119.

STATEMENT REGARDING FEDERALLY SPONSORED RESEARCH AND DEVELOPMENT

This invention was made with Government support under Grant No. HR0011-06-1-0050, awarded by the DOD/DARP. The Government has certain rights in this invention.

TECHNICAL FIELD

The technical field generally relates to devices and methods that can accurately detect and quantify nucleic acids over an extremely high dynamic range from a sample volume. The invention can also be used for disease detection, water monitoring purposes and more.

BACKGROUND

Lab on a chip devices continuously strive to provide more information and function in ever smaller packages. This becomes evident when considering the growth of on-chip microarrays and micro/nanoreactors for massively parallel or high-throughput processing. On-chip nanowells and droplet reactors have gained attention in the field of digital biology for applications like single-cell analysis and single-copy nucleic acid detection including: digital quantification of DNA, monoclonal template amplification for bead-based gene sequencing, reverse transcriptase (RT-PCR) for detection of single RNA fragments, and multiplexed digital PCR. Digital PCR platforms benefit from each reactor having its own microenvironment where the amplification in one reactor does not interfere with that of another. This provides a digital output of nucleic acid concentrations with increased quantitative resolution.

Furthermore, single DNA molecules can be quantified even in the presence of competing template sequences, which would otherwise skew traditional qPCR results. Unfortunately, the dynamic-range of on-chip digital PCR lags behind its analog counterparts by three to four orders of magnitude due to the lack of compartmentalized reactors and limited volume throughput. This is further compounded by Poisson distribution behavior of single molecule encapsulation, which requires low concentrations of DNA relative to reactor number. In addition, many nucleic acid processing schemes benefit from real-time fluorescence measurements, which provide temporal information about PCR amplification, but few high throughput platforms provide this ability.

A prior method that has been used was to compare the stoichiometric amplification efficiency of PCR and determine the initial concentration based on cycle number when fluorescence exceeded a threshold value. Another approach that has been used was monitoring real-time PCR amplification of nucleic acids to estimate amplification based on intrinsic amplification rates corresponding to the amount of time or number of cycles over which replication occurred. As described below, the device and methods described herein are able to yield significantly higher dynamic ranges with exceptionally higher resolution and accuracy than any prior methods.

BRIEF DESCRIPTION OF THE DRAWINGS

FIG. 3 schematically illustrates the range of digital PCR and real time PCR (e.g., qPCR) as a function of initial copy number.

SUMMARY

In one embodiment, a method is disclosed wherein nucleic acids are encapsulated into many small reactions volumes that are then imaged in real-time over the course of a nucleic acid amplification process to enable both digital and analog quantification of nucleic acid concentration.

While amplification of the nucleic acid is performed, one or all reaction volumes are fluorescently monitored in real-time to determine quantitative real-time analysis of initial nucleic acid concentration. The initial nucleic acid concentration may be determined based on the cycle threshold (Ct) of one or more droplets during this real-time monitoring. In addition, all reaction volumes are fluorescently analyzed at least once for end-point detection to determine the number of positively amplified reaction volumes to determine digital amplification analysis of initial nucleic acid concentration. The initial nucleic acid concentration is then determined as a function of both the number of fluorescent reaction volumes amplified, therein comprising a digital PCR quantification for low copy number samples; and real-time analysis of average reaction volume amplification thresholds for high copy number samples. The use of Stoichiometric analysis aids in predicting the total initial nucleic acid concentration as an additive effect of the number of amplified reaction volumes, combined with the average cycle threshold of one or all amplified reaction volumes. Nucleic acids can consist of DNA, RNA, and other variants. Amplification techniques can consist of polymerase chain reaction, reverse-transcription, or other variants.

Multiple individual reaction volumes are used to discretize a standard nucleic acid sample volume into many smaller reaction volumes. The sample discretization can be achieved using standard droplet/emulsion techniques. Alternatively, sample discretization can be achieved in micro/nanowell techniques without the need for droplets. Nucleic acid amplification is performed inside of all reactors and a fluorescent or other type of detectable marker is used to quantify the rate and amount of nucleic acid amplified within each reaction volume. In the case where fluorescent probes are utilized to indicate nucleic acid amplification, the overall fluorescence level of at least one, but preferably all reaction volumes are monitored as a function of nucleic acid amplification cycle to determine both a digital signal of present or not present samples, and the amplification rate to determine how much is present in each droplet if concentration exceeds the digital regime. Each reaction volume contains sufficient nucleotides, primers, polymerase enzyme, DNA sequence specific fluorescent probes and buffer to amplify and detect target specific nucleic acids. For the digital regime, fluorescence detection is performed to image the ratio or percentage of droplets which fluoresce as a function of the target specific fluorescent probe. At copy or concentration numbers higher than the digital regime, an initial concentration of nucleic acid in the sample is based on a cycle threshold (Ct) obtained of one or more droplets within the array.

This device can yield digital qPCR results of large sample volumes (50 uL) from a range of as little as one single nucleic acid strand to as high as is stoichiometrically determined based on reaction volume, size and number, or as much as is practically limited based on the precipitation concentration of DNA sample. The smaller the reaction volume and greater the number of discrete volumes, the higher the concentration limit that can be detected, the larger the total reaction volume the lower the concentration limit that can be detected.

An advantage of the current invention is that it can yield significantly higher dynamic ranges with exceptionally higher resolution and accuracy than any prior methods employed. Digital PCR analysis techniques enable extremely high accuracy and limits of detection in low concentration reactions. Real-time PCR analysis enables an extension of the dynamic range of the digital PCR amplification; in addition there is an extremely high number of replica's in the number of reactions allowing for exceptionally high accuracy in estimating real-time quantitative results to higher degrees of accuracy than typically possible using the typical 3-replica approach performed in standard analysis protocols.

In one embodiment, a method of quantifying nucleic acids in a sample includes generating a plurality of droplets in oil within a microfluidic device, wherein at least some of the droplets comprise a nucleic acid, amplification reagents, and a fluorescent probe or dyes contained therein. The droplets are delivered to a collection chamber to form an array of droplets. The droplets are subject to thermal cycling within the collection chamber a plurality of times to perform nucleic acid amplification within the droplets. The array of droplets is imaged during the plurality of thermal cycles as well as at a thermal cycle endpoint. An initial concentration of nucleic acid in the sample is calculated based on at least one of: a ratio of aqueous phase droplets exhibiting fluorescence within the array at the thermal cycle endpoint or a cycle threshold (Ct) of one or more aqueous phase droplets within the array.

In another embodiment, a system for quantifying nucleic acids in a sample includes a microfluidic droplet generating device, the microfluidic droplet generating device comprising a droplet generating region formed by an intersection of pinching oil channels and an aqueous reagent channel, a plurality of droplet splitting branch channels, and a collection chamber dimensioned to receive a two dimensional array of droplets. The system includes a thermal cycler in thermal communication with the collection chamber of the microfluidic chamber and an illumination source configured to illuminate the array of droplets with excitation light. The system includes an imaging device focused on the array of droplets, the imaging device capturing fluorescent radiation emitted from droplets contained in the collection chamber, and at least one processor configured to calculate an initial concentration of nucleic acid in the sample based on at least one of: a ratio of droplets exhibiting fluorescence within the array at a thermal cycle endpoint or a cycle threshold (Ct) of one or more droplets within the array.

DETAILED DESCRIPTION OF ILLUSTRATED EMBODIMENTS

Figure 1A:
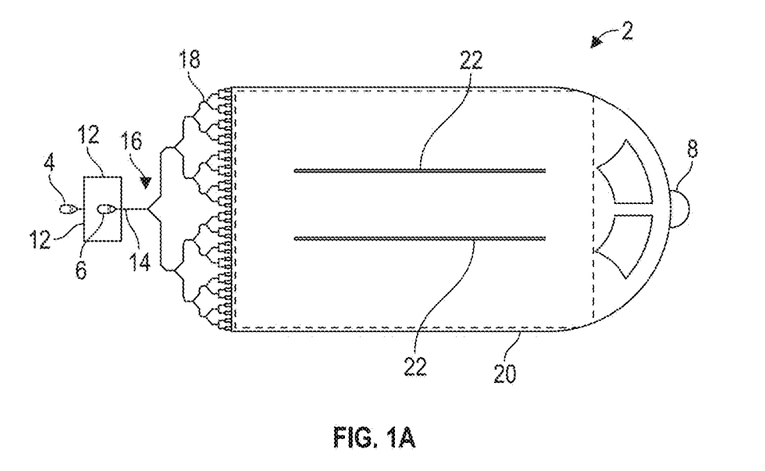
FIG. 1A illustrates a microfluidic device for splitting droplets containing amplification (e.g., PCR) reagents according to one embodiment. Droplets containing the nucleic acid of interest as well as any amplification reagents generated using a pinching flow from oil. Droplets are collected in a downstream viewing chamber.

FIG. 1A illustrates a microfluidic device 2 according to one embodiment that is used as part of a system that measures or quantifies the amount of nucleic acid in a sample. The microfluidic device 2 includes an oil inlet 4, an aqueous phase inlet 6, and an outlet 8. As explained herein, the microfluidic device 2 is used to generate a plurality of aqueous phase droplets 10 (see FIGS. 2, 4, 7A-7C) that are observed for their fluorescent light emission which is used to calculate the amount of nucleic acid in the sample. The oil inlet 4 is coupled to a source of oil that is pumped (e.g., using pumps (not shown)) or otherwise flowed into the device during the droplet generation process. Different types of oil may be used (e.g., mineral oil). The aqueous phase inlet 6 is coupled to the sample source as well as the reagents used during the nucleic acid amplification reactions that take place within the droplets 10. The sample and reagents may be pumped (e.g., using pumps (not shown)) or otherwise flowed into the inlet 6. The reagents may include nucleotides, primers, polymerase enzymes, nucleic acid sequence-specific fluorescent probes and buffer(s) that are used during the amplification reaction. As seen in FIG. 1A, the oil inlet 4 splits between two channels 12 that then intersect in a pinching arrangement with a channel 14 that is coupled to the aqueous phase inlet 6. This intersection of the channels 12, 14 forms the droplet generation region 16 whereby aqueous phase droplets 10 are formed within the oil carrier. The generated droplets 10 then pass into a cascading series of droplet splitters 18. Each generation of droplet splitters 18 doubles the number of droplets. In the microfluidic device 2 of FIG. 1A, there are eight (8) generations of droplet splitters 18. Thus, a single droplet 10 is split into 256 separate droplets 10. These smaller, split droplets 10 then pass to a collection chamber 20 that is used to hold the generated droplets 10 within an array. The collection chamber 20 is a three dimensional volume and may include optional vertical supports 22 to ensure the structural integrity of the collection chamber 20 and to ensure a uniform height. The collection chamber 20 is preferably made from and optically transparent material so that fluorescent light emitted by the fluorescent probes within the droplets 10 can be imaged.

In one illustrative embodiment, the collection chamber 20 has a width of 27 mm and a length of 40.5 mm. The height of the collection chamber 20 is 78 μm. These dimensions, however, are illustrative and may vary. The height of the chamber 20 is such that the droplets 10 will form a packed array of droplets 10 when stored therein. In some embodiments, the droplets 10 will form a two-dimensional array of droplets 10. In other embodiments, the droplets 10 will form a three-dimensional array of droplets 10. For example, the droplets 10 may exhibit square packing (100) lattice orientations or hexagonal packing (111) configurations. It should be understood that the volume and dimensions of the collection chamber 20 may vary. A larger volume of the collection chamber 20 will hold a larger numbers of droplets 10 and, for example, expand the dynamic range of digital PCR regime. Likewise, by having a larger number of droplet splitters 18 there are a larger number of small droplets 10 that can form which again expanded the upper end of dynamic range for the digital PCR regime. While in some embodiments, one may want to have a large number of droplets 10 (e.g., over 1 million) being formed in the collection chamber 20, the invention is not so limited. In one embodiment, the droplets 10 may be sized within the range of 40-60 μm and have volumes within the range of 40-80 pL. Collectively, the chamber may hold about 15 μL of sample solution, although other volumes and droplet sizes are contemplated.

Figure 1B:
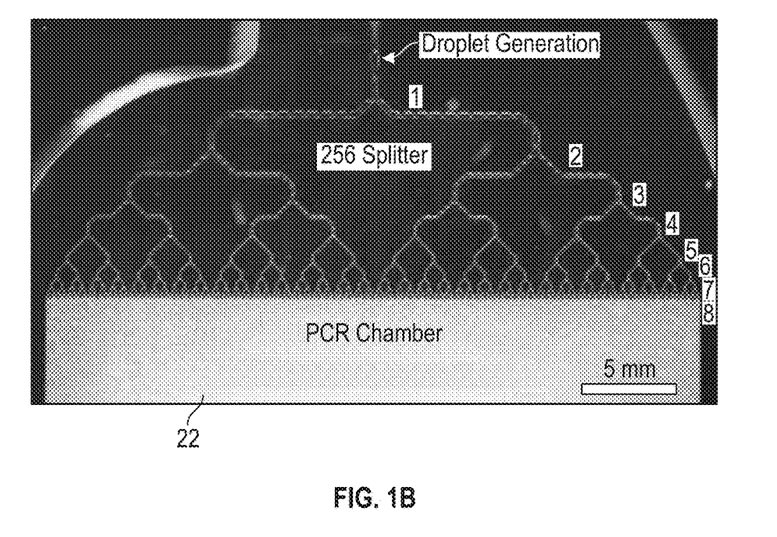
FIG. 1B illustrates a photographic image of portions of the microfluidic device illustrated in FIG. 1A. Eight generations of droplet splitters are illustrated that create a 256 splitter configuration. A portion of the collection chamber where amplification takes place (e.g., PCR chamber) is also illustrated.

FIG. 1B illustrates a photographic image of a portion of the microfluidic device 2 illustrated in FIG. 1A. Eight generations of droplet splitters 16 are illustrated that create a 256 splitter configuration. Again, the number of generations of droplet splitters 16 may be adjusted depending on the desired end number/size of the droplets 10. A portion of the collection chamber 20 (e.g., PCR chamber) is also illustrated. The collection chamber 20 holds the droplets 10 that are generated by the droplet generation region 16. The droplets 10 within the collection chamber 20 can be removed from the microfluidic device 2 using the outlet 8.

During use, droplet 10 generation (droplets 10 are illustrated in FIGS. 4 and 7A-7C) may be achieved flowing the sample and amplification reagents (e.g., PCR reagents) into the aqueous inlet 6 while oil (heavy white mineral oil (Fisher Scientific)) is fed into the oil inlet 4. In the device of FIG. 1A, the droplet generation region 16 generates a large 13 nL parent droplet (not illustrated in FIG. 1A) although other sized droplets can be formed. This droplet then split eight (8) times to form 256 daughter droplets. High w/o volume ratios and stable droplet generation can be achieved using heavy white mineral oil (Fisher Scientific) combined with the stabilizing surfactants 3% w/w Abil EM 90 (Degussa/Goldschmidt) and 0.1% w/w Triton X-100 (Sigma-Aldrich). The first parent channel was designed with a width of 240 μm followed by eight (8) bifurcation junctions at 45° angles, with √2 width reductions between junctions 2 and 7, resulting in a final width of 30 μm at the outlet.

Droplet generation rates may vary but a typical flow rate may include 8 μL min$^{-1}$ PCR solution and 4 μL min$^{-1}$ oil; resulting in droplet generation frequencies of 2.66 kHz and 66% water/oil (w/o) volume ratios. Faster flow rates up to 25 μL min$^{-1}$ PCR solution and 25 μL min$^{-1}$ oil may also achieved resulting in a droplet generation frequency of 8.33 kHz and a 50% w/o volume ratio. W/o volume ratios ranging between 50% and 66% are favorable for various high-density single or double-layer droplet array packing configurations.

Figure 1C:
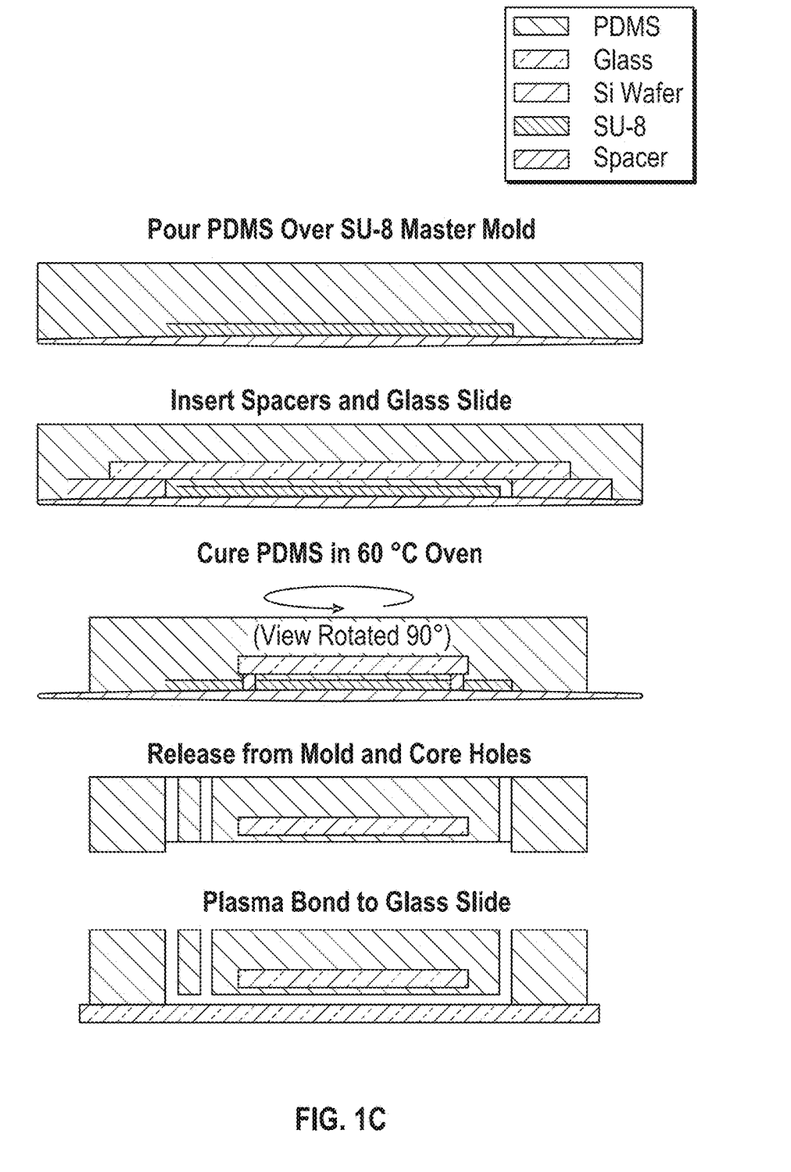
FIG. 1C illustrates an illustrative process that is used to fabricate the microfluidic device of FIG. 1A.

The microfluidic device 2 of FIG. 1A may be fabricated using conventional microfluidic manufacturing processes. For example, polydimethylsiloxane (PDMS) may be patterned using standard soft lithography processes as illustrated in FIG. 1C. This PDMS cast may then be bonded to a substrate such as glass to form the device 2. For example, single-height microfluidic master molds of 78-80 μm thick SU-8 structures were fabricated on 3 inch silicon wafers in a clean-room facility. Sylgard-184 PDMS (Dow Corning) was cast on top of the SU-8 molds and a 1 mm thick glass slide cut to 2 inch×2 inch was embedded inside the PDMS layer spaced 225 μm above the viewing chamber using 30 awg Kynar wire. The embedded glass vertical supports 22 served to reduce deformation of the microfluidic chamber and create a vapor barrier to reduce oil and PCR reagents from evaporating during PCR thermocycling. The PDMS was then cured in a 60° C. oven for 4-6 hours, released from the mold, inlet and outlet holes were cored, then bonded to 1 mm thick 2 inch by 3 inch glass slides (Corning, USA) using air plasma treatment (Harrick Plasma, USA). Finally, the entire device was placed in a 120° C. oven overnight to return the material to its native hydrophobic state. FIG. 1A shows the mask design used to pattern the SU-8 molds.

Figure 2:
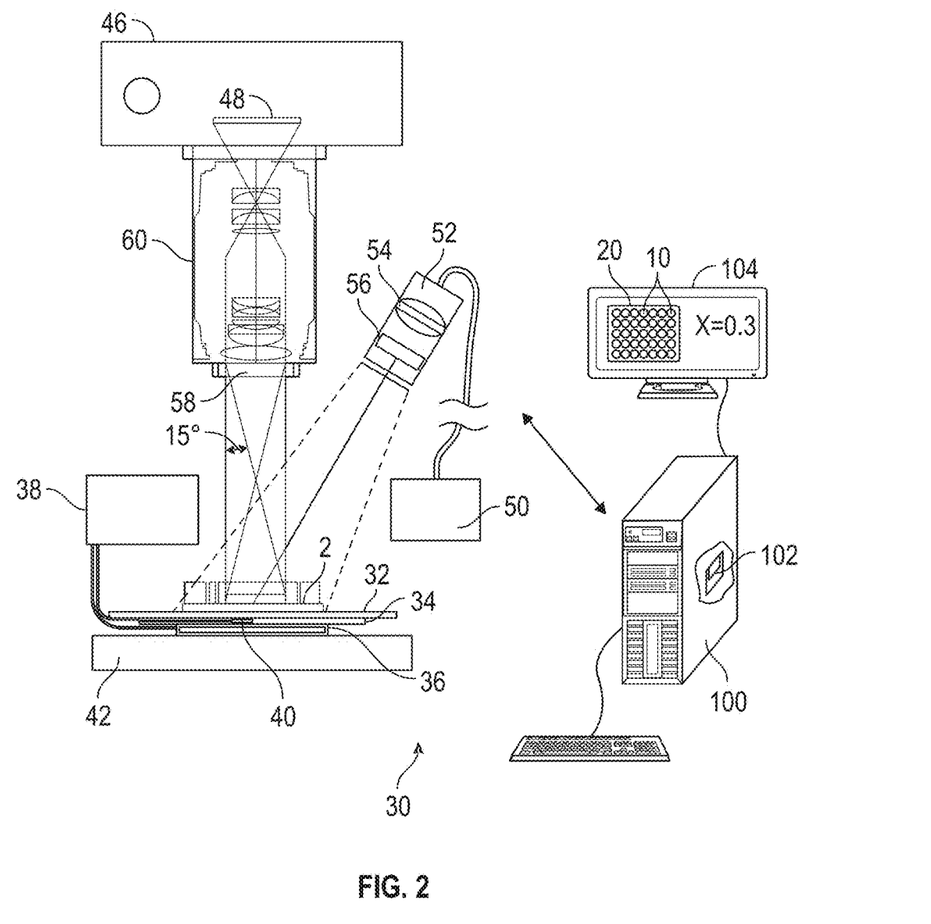
FIG. 2 illustrates a wide field-of-view fluorescent imaging setup according to one embodiment. The system includes an associated computing device that is used to run software to measure the initial concentration in a sample using either a digital mode or a real time detection mode.

FIG. 2 illustrates the setup of a system 30 that may be used to thermocycle the temperature of the collection chamber 20 as well as image the fluorescent light that is emitted from the droplets 10. As seen in FIG. 2, the microfluidic device 2 is disposed atop a silicon wafer 32 that is in thermal contact with a copper plate 34. Thermocycling of the microfluidic device 2 for amplification can be achieved using a thermocycler 36 such as, for example, a 39.7 mm×39.7 mm thermoelectric cooler (TEC). The TEC 36 is controlled using a thermocycle controller 38 such as a FTC-100 controller (Ferrotec Inc., USA) which is controlled using manufacturer-supplied software. Alternatively, the TEC 36 may be controlled using the computing device 100 as discussed herein.

Temperature feedback control can be accomplished by inserting the 1 mm thick 2 inch×2 inch copper plate 34 between the microfluidic device 2 and TEC unit 36 with an embedded TR-1(2245) thermistor 40 (Ferrotec Inc., USA). A waste heat block 42 is placed beneath the TEC device 36 to dissipate waste heat. The waste heat block 42 was a custom-fabricated liquid cooled aluminum block although other heat dissipation devices may be used. As noted a 3 inch silicon wafer 32 can be placed between the copper plate 34 and microfluidic device 2 to help equalize heat distribution and provide a better optical surface for imaging.

The microfluidic device 2 and droplets 10 formed thereby may be used to amplify nucleic acids (e.g., DNA or RNA). Amplification may use PCR or reverse transcription or alternative amplification schemes. For a PCR-based amplification scheme, reagents may be prepared using stardard protocols (e.g., Amplitaq Gold Fast PCR Master Mix UP (2×) PCR kit (Applied Biosystems). The PCR reagent solution includes, in addition to the sample DNA, forward/reverse primer pairs, fluorescent labeled probes (e.g., 6-carboxyfluorescein, FAM). BSA may be added to the solution to reduce surface adsorption of DNA or enzymes to surfaces and further stabilize the emulsion and PCR.

In the case of PCR amplification, two-step PCR thermocycling can be initiated with a 10 minute "hot start" at 95° C. to activate the Taq-polymerase then 40-45 cycles of ramping between 58° C. and 95° C. using 30 second hold times and 2-3° C. $s^{-1}$ thermal ramp rates. The total PCR thermocycling reaction time required ~65 minutes. The ability to perform on-chip thermocycling of droplets was necessary to be able to perform real-time observation of the entire droplet reactor array during PCR amplification.

Still referring to FIG. 2, images of the droplets 10 may be obtained using a Canon 5D Mark II digital single lens reflex (dSLR) camera 46 with a 21 megapixel CMOS sensor 48 and a 100 mm f/2.8 USM Macro Lens (Canon Inc., USA). The dSLR camera 46 and macro lens 60 can be mounted to a photocopy stage and positioned 6 to 8 inches above the thermocycling setup with the microfluidic device 2 on top as illustrated. Fluorescence imaging ability is added using an Omniprint-1000 350W portable light source 50 with a 3 mm fiber-optic cable (Omnichrome, USA) coupled to a fiber optic wand 52 with focusing objective 54 and an excitation filter 56 that is placed 5-8 inches above the device, at a 30-45° angle, to illuminate an area 1 cm wider than the chamber's longest diagonal or ~5 to 6 cm. An emission filter 58 can be positioned on the front of the camera lens 60 (100 mm macro focus lens). For the excitation filter 56 and emission filter 58, a commercial GFP-3035 Brightline® filter set (Semrock, USA) can be used (25 mm excitation filter 56 and 32 mm emission filter 58).

The macro-fluorescence imaging setup is capable of imaging 8.6-17.2 $cm^2$ areas at 1× to 0.5× magnification, respectively. The Canon 5D Mark II sensor contains a 36 mm×24 mm 3:2 format 3 color RGB CMOS sensor in an RGBG Bayer mosaic filter pattern with 6.4 mm pixel pitch and individual microlenses per pixel providing greater quantum efficiency. Image capture settings can typically be taken at f/2.8 aperture, ISO 400-800, 0.85× magnification, ~6.5 inch working distance, and 4-8 s exposure in RAW image format with long exposure noise reduction enabled. The 100 mm macro-lens 60 provides a 600 working focal distance from the front of the lens 60 to the imaging plane and a focal depth of >100 mm at f-number, f/2.8 and 1× magnification. At this focal length, the camera 46 has an equivalent numerical aperture, NA, of ~0.089. With these imaging parameters, 20-40 pixels per droplet resolution could be achieved for a 1-million droplet array packed within collection chamber 20.

FIG. 2 illustrates a computing device 100 that is used as part of the system 30. The computing device 100 may include, for example, a personal computer, laptop computer, tablet computer, or the like. The computing device 100 includes one or more processors 102 therein that are configured to run software to calculate the initial copy number or concentration in a sample using either the digital mode 70 or the real time mode 72 (or both) as described herein. The one or more processors 102 also run imaging software (which may incorporate the calculation functionality) that is used to acquire the images of the droplets 10 in the collection chamber 20 and used to identify "positive" droplets 10 as well as determine at what cycle droplets 10 emit fluorescent light above a pre-determined threshold intensity. The imaging software as described herein is able to identify those "positive" fluorescent light-emitting droplets 10 and count the ratio or percentage of those droplets 10 as compared to the total number of droplets 10. In the real time mode 74, the imaging software also tracks individual droplets 10 from frame to frame so that the same droplets 10 are looked at to see when their respective fluorescence levels cross the threshold value.

The computing device 100 generates an initial copy number or concentration based on this ratio or percentage based on a Poisson distribution when the device operates in the digital mode 70. When the device is in the real time mode 72, the imaging software analyzes a single droplet 10 or multiple droplets 10 to determine when their respective fluorescence level crosses a particular threshold level. The cycle or intra-cycle point at which this cross-over is reached is then used to calculate or derive an initial copy number or concentration.

The computing device 100 may also interface with and operate various aspects of the system 30. For example, the computing device 100 may operate the light source 50, camera 46, thermocycle controller 38, pumps, and the like. The computing device 100 also includes a display 4 that can be used to display, for example, data and results to the user. For example, FIG. 2 illustrates the display 104 presenting an image of the droplets 10 in the collection chamber 20 along with the measured ratio of positive droplets 10. Of course, other data and results can be displayed to the user on the display 104 is this is just one illustrative example.

Figure 3:
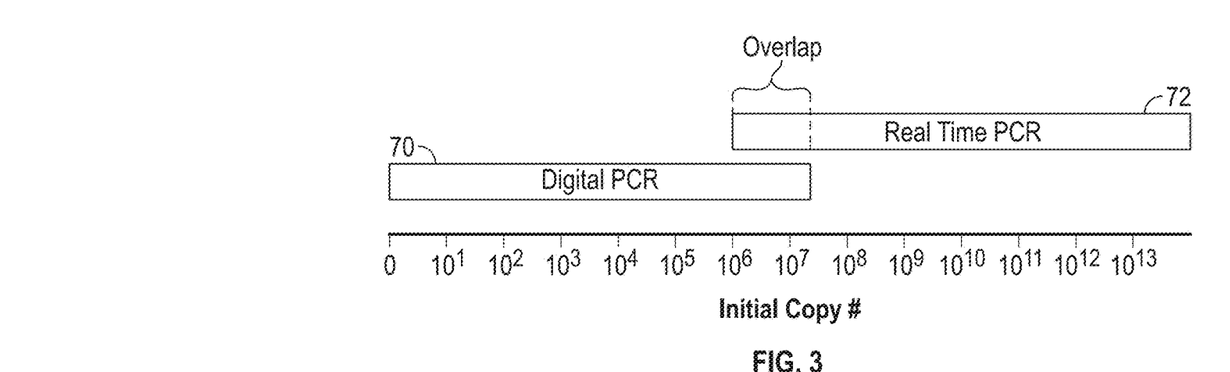
As seen in FIG. 3, digital PCR is accurate when low copy numbers are present in the sample. Conversely, real time PCR is accurate a high copy numbers. In this example, there is an overlap region where the two modes both produce reasonably accurate results.

FIG. 3 illustrates how the present invention works according to one embodiment of the invention. As seen in FIG. 3, the method of quantifying nucleic acid in a sample includes two different modes of operation. In a first mode of operation, the system operates in a digital mode 70 (e.g., digital PCR). In a second mode of operation, the system operates in a real time mode 72 (e.g., real time PCR). The first mode has particular accuracy and suitability where nucleic acid concentrations are low, namely, where droplets 10 that are created by the microfluidic device 2 have a generally low copy number. In this example, the first mode 70 has good or acceptable accuracy from a single copy per droplet 10 up to around $10^7$ copies per droplet 10. As one nears this upper limit, the accuracy of the digital mode 70 decreases. Still referring to FIG. 3, the second mode of operation is more suitable for higher concentrations of nucleic acid, namely, where droplets 10 that are created by the microfluidic device 2 have a generally high copy number. In this example, the second mode 72 has good or acceptable accuracy from around $10^6$ copies per droplet 10 to around $10^{13}$ copies per droplet 10. At lower copy numbers, the real time mode 72 is less accurate than at higher copy numbers.

Note that as seen in FIG. 3, there is an overlap between the digital mode 70 and the real time mode 72. In some embodiments of the invention, when one operates in this overlap region, the digital mode 70 is chosen over the real time mode 72. In an alternative embodiment, the real time mode 72 is chosen over the digital mode 70 when in an overlap condition. In still another embodiment, both the digital mode 70 and the real time mode 72 may be used and reported to the user when in this overlapping state. In still yet another alternative, the results from the different modes 70, 72 could be combined, for example, using an average or the like.

In the digital mode 70, the array of droplets 10 is imaged at a thermal cycle end point (e.g., after each thermal cycle or after many thermal cycles) and the number of "positive" droplets 10 are counted and compared to the total number of droplets 10. This may be expressed as a ratio or a percentage. Positive droplets 10 are those droplets 10 that emit fluorescence light. A threshold fluorescence level may be used to determine whether a particular droplet 10 may be considered "positive." Once one has obtained the positive fraction of droplets 10 the fraction can then be translated into a concentration or copy number of nucleic acid in the fractionated sample. This is because in the digital mode 70 regime, according to Poisson's law of small numbers, a Poisson distribution can be used to determine the number of nucleic molecules in each droplet. Generally, the average number of nucleic acid copies per reaction volume (i.e., droplet 10) can be determined by the formula —ln(1-x) where x is the fraction of positive droplets 10 to the total number of droplets 10.

Figure 4:
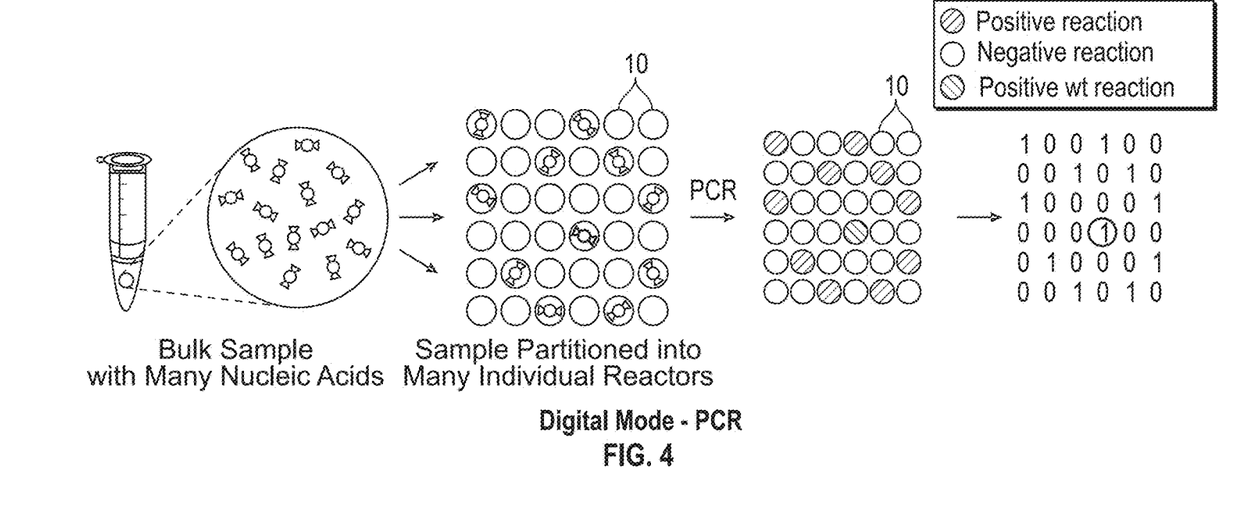
FIG. 4 schematically illustrates operation of the digital mode for PCR amplification.

FIG. 4 illustrates a schematic illustration of the process of digital PCR being performed on a bulk sample having many nucleic acids therein. The sample is partitioned into separate reactors in the form of droplets 10 using the microfluidic device 2 described herein. The droplets 10 then undergo PCR amplification. After a plurality of cycles, the droplets 10 are then imaged using the system 30 described herein. The droplets 10 that emit fluorescent light are deemed positive droplets 10. A digital readout of the droplets 10 is generated where each droplet 10 is characterized either as positive (1) or negative (0) as illustrated in FIG. 4. The ratio (or percentage) of positive droplets 10 (e.g., "x") is then readily calculated. Note that different fluorophores or dyes may be used to amplify different sequences of nucleic acid. For example, in FIG. 4 ten drops are positive with respect to one fluorophore or dye and one drop is positive using a different fluorophore or color. Each different "color" of fluorophore or dye may be specific to a different sequence. Thus, multiplex testing may be used in the system 30.

Various software programs can be used to aid in analyzing the array of droplets 10 for the digital PCR measurements. For example, ImageJ software using Matlab code may be used by the computing device 100 to detect and quantify fluorescent droplets 10 and analyze their size, packing geometry (e.g., when multiple layers are formed in the collection chamber 20), density and fluorescence intensity. For example, reference is made to the methods disclosed in Hatch et al., 1-Million droplet array with wide-field fluorescence imaging for digital PCR, Lab Chip, 2011, 11, 3838-3845, which is incorporated by reference herein. Software can be used to perform background subtraction, contrast enhancement, and flatfield corrections. In one aspect, a first level background correction may be performed using the camera's 46 own peripheral illumination correction and long-exposure noise correction. For digital PCR quantification of positive droplets 10, Fast Fourier Transfer (FFT) filtering may be used to filter out unwanted spatial frequencies in intensity. This permits the use of thresholding or local maxima detection schemes to quantify the digital PCR results. Positive droplets 10 may be detected using a maximum entropy or Otsu's method of thresholding and then their intensity measured from the original image. See P. K. Sahoo et al., Comput. Vision Graphics Image Process., 1988, 41, 233-260, which is incorporated by reference herein. FFT analysis can be used to determine droplet lattice orientation and average droplet size.

Figure 5:
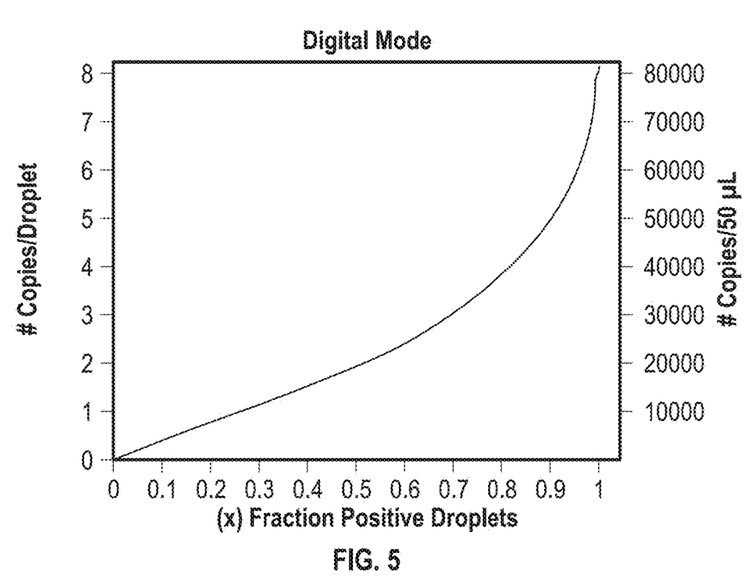
FIG. 5 illustrates a Poisson distribution showing number of copies per droplet/number of copies/volume as a function of the fraction of positive droplets (x). This is used for the digital mode.

FIG. 5 illustrates an example of a Poisson distribution of digital PCR data. The curve represents the relationship between the fraction of positive droplets 10 and the number of nucleic acid copies per droplet. The number of nucleic acid copies per droplet can also be expressed as the total number of copies in a certain volume of sample (e.g., 50 µL). As seen by the Poisson distribution of data, one can determine the initial amount or concentration of nucleic acid based on the ratio or percentage of positive droplets 10. A higher number of droplets 10 results in more accurate Poisson-based counting. In addition, as noted herein, digital PCR is accurate and most effective at low copy numbers. At higher fraction numbers, for example, at ratios higher than 0.8 digital PCR is less accurate. Nonetheless, the digital PCR mode 70 may be used to determine initial copy numbers or concentration over a range from 1 copy to about $10^7$ copies although this range may vary.

Figure 6A:
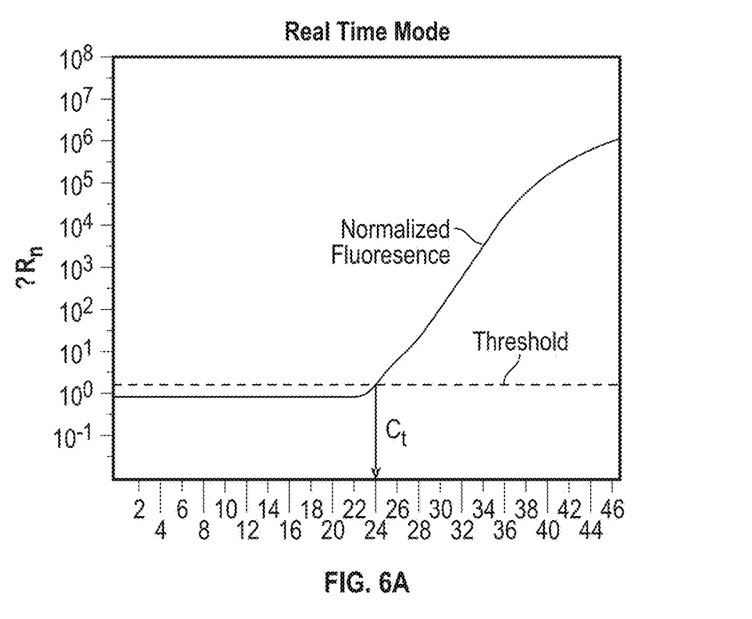
FIG. 6A illustrates a graph of baseline-subtracted fluorescence signal as a function of amplification cycle. The threshold fluorescence value is illustrated along with the threshold cycle (Ct); the cycle number at which fluorescence signal crosses the threshold value.
Figure 6B:
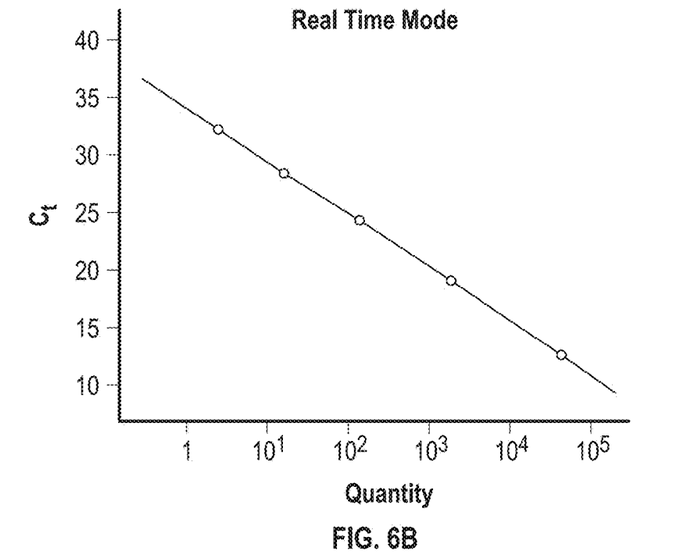
FIG. 6B illustrates a standard calibration curve illustrating the threshold cycle (Ct) as a function of starting quantity of nucleic acid.

FIGS. 6A and 6B illustrates aspects of how initial copy number or concentration is determined using the real time PCR mode 72. In the real time PCR mode 72 the fluorescence of one or more droplets 10 is monitored temporally during the amplification process. For example, the fluorescence of the droplets 10 is monitored at the beginning and end of a particular thermal amplification process; and may also be monitored in between the beginning and end of a thermal cycle. In real time PCR mode 72, the fluorescent signal from the droplets 10 is monitored as a function of the cycle number (or fraction thereof). Reactions are characterized by the point at which during cycling when the amplification of a nucleic acid reaches a threshold limit. The higher the starting copy number of nucleic acid, the more quickly (less cycles) a significant increase in fluorescence signal is recognized. A threshold fluorescence detection level is established that is used to calculate the initial copy number of nucleic acid. The threshold level is set above a baseline but is low enough to be within the exponential growth region of the amplification curve. Typically, amplification is performed with a reporter dye and a passive reference dye that acts as an internal reference to which the reporter dye signal can be normalized. Normalization corrects for variations in fluorescent fluctuations caused by volume changes and other conditions. FIG. 6A illustrates a graph showing a background-corrected fluorescence signal as a function of cycle number. Also illustrated in FIG. 6A is the threshold value. FIG. 6A illustrates the threshold cycle (Ct) which is the cycle number (or fractional cycle number) at which the fluorescent signal crosses the threshold. The Ct is used to calculate the initial nucleic acid (e.g., DNA) copy number as Ct is inversely related to the starting amount of nucleic acid. In the example illustrated in FIG. 6A, the normalized fluorescence level crosses the threshold at cycle number 24. Thus, the Ct in this example is 24.

FIG. 6B illustrates how a Ct value can then be correlated to an initial nucleic acid copy number. FIG. 6B illustrates a standard calibration curve showing how Ct values correlate to nucleic acid quantity (either copy number in droplet 10 or in sample). According to one aspect of the invention, once the Ct value is obtained, the initial nucleic acid copy number or amount can then be determined by using the calibration curve. This calibration curve may be stored in the computing device 100, processor 102, or memory as a look up table or a function whereby the concentration can be readily determined. Note that the Ct value that is measured may correspond to a single droplet 10 or it may correspond to multiple droplets 10. For example, in one embodiment of the invention, a plurality of droplets 10 may be observed and a Ct value calculated for each droplet 10 and an average Ct is calculated for the plurality. This average Ct value is then compared to the calibration curve to then identify the initial copy number or amount.

Figure 7A:
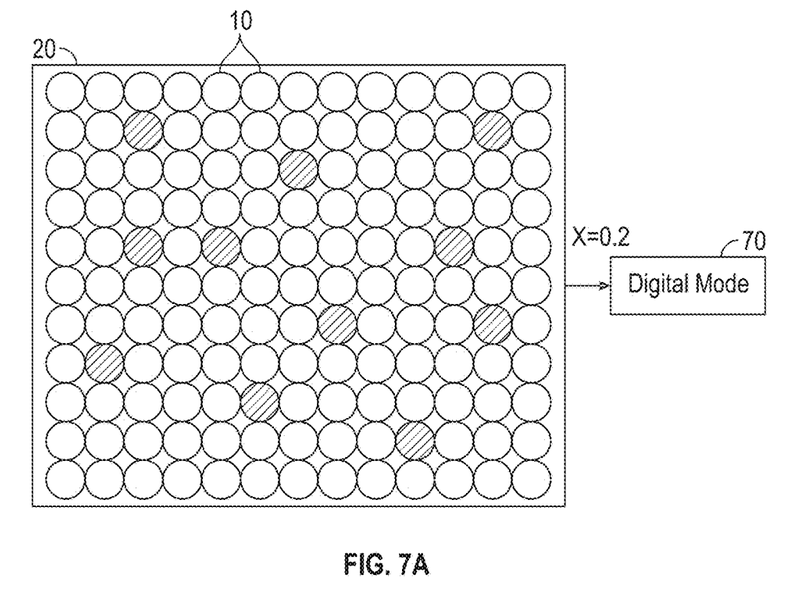
FIG. 7A illustrates an image of a portion of the collection chamber containing an array of droplets. In this illustration, about 20% of the droplets are positive. Based on the low % of positive droplets, the system operates in the digital mode.
Figure 7B:
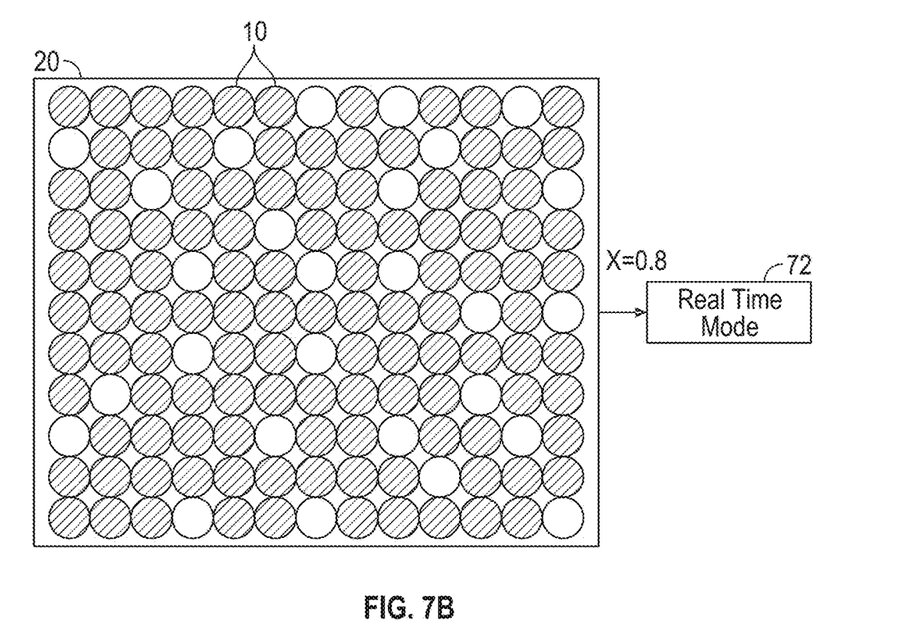
FIG. 7B illustrates an image of a portion of the collection chamber containing an array of droplets. In this illustration, about 80% of the droplets are positive. Based on the high % of positive droplets, the system operates in the real time mode. In some embodiments, both modes may be used in this range.
Figure 7C:
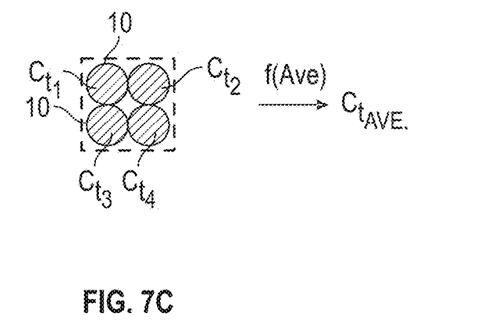
FIG. 7C illustrates how four (4) droplets are monitored for their respective Ct values and averaged to produce an average Ct result that is used in the real time mode.

FIGS. 7A illustrates a schematic view of a selected sub-region of an array of droplets 10 whereby the system 30 operates in the digital mode 70. The system 30 operates in the digital mode 70 because, based on the number of positive droplets 10 (x=0.2), this is a regime where the digital mode 70 has high accuracy to determine the initial copy number. Because there are a low number of positive droplets 10, use of the real time mode 72 would not generate accurate results. As explained above, the Poisson distribution (FIG. 5) is used to determine the number of initial copies. FIG. 7B illustrates a schematic view of a selected sub-region of an array of droplets 10 whereby the system 30 operates in the real time mode 72. In contrast to FIG. 7A, there are a significant number of positive droplets 10 in the array (x=0.8). This is indicative of a high number of copies of nucleic acid. Because of the high ratio of positive droplets 10 in the sample, the system 30 operates in the real time mode 72. In the real time mode 72, as explained above, the cycle threshold (Ct) is used to determine the initial copy number. In one embodiment, a single representative positive droplet 10 may be used to determine the Ct value which can then be converted into an initial copy number. In another embodiment, as illustrated in FIG. 7C, multiple droplets 10 imaged and their respective Ct values are obtained (Ct1, Ct2, Ct3, Ct4) and these values are then averaged to compute an average Ct value ($Ct_{AVE}$). While four (4) such droplets are averaged it should be understood that larger (or fewer numbers) of droplets 10 may be used.

In one particular embodiment of the invention, a method for quantifying nucleic acid in sample includes the operation of generating a plurality of aqueous phase droplets in oil within a microfluidic device, wherein at least some of the aqueous phase droplets 10 that include a nucleic acid, amplification reagents, and a fluorescent probe contained therein. For example, the amplification reagents may include PCR reagents when the nucleic acid is DNA. The plurality of aqueous phase droplets 10 that are generated are delivered to a collection chamber 20 to form an array of droplets 10 contained therein. Next, the aqueous phase droplets 10 undergo thermal cycling within the collection chamber a plurality of times to perform nucleic acid amplification within the droplets 10. As the droplets 10 undergo thermal cycling, the array of droplets 10 are imaged a plurality of times. For example, they may be imaged at the beginning, end, and intermediate time points within a single thermal cycle. Within any particular thermal cycle at least one a thermal cycle endpoint image is obtained of the droplets (e.g., at end of cycle). This image is then used to identify the ratio or percentage of positive droplets 10 in the chamber 20 or field of view.

Based on the ratio or percentage of positive droplets 10, either the digital mode 70 or the real time mode 72 will be activated. For example, if the ratio of positive droplets 10 is less than or equal to 0.8 then the system 30 will operate presumptively in the digital mode 70. If the ratio of positive droplets 10 is more than 0.8 then the system 30 will operate in the real time mode 72. It should be understood that the cutoff value of 0.8 may be changed (either higher or lower). For example, in some instances, the digital mode 70 may provide accurate results up to a ratio of 0.9. If the system 30 is using the digital mode 70, the initial concentration (or copy number) of nucleic acid is calculated by looking at the ratio of positive droplets 10 as explained herein. If the system 30 is using the real time mode 72, the initial concentration (or copy number) of nucleic acid is calculated by looking at the cycle threshold (Ct) of one or more droplets 10.

As noted above and seen in FIG. 3, there is a range of overlap where both digital PCR and real time PCR yield accurate results. In one embodiment, calculated initial copy numbers may be provided using both the digital mode 70 and the real time mode 72. For example, if the overlap region generally applies to copy numbers within the range of $10^6$ to $10^7$, then according to this embodiment, both numbers will be provided to the user. In yet another embodiment, the results from both modes 72, 74 may be combined into a single number using an average for example.

In another embodiment of the device, various predictive algorithms may be used to determine whether the digital mode 70 or the real time mode 72 will be used. For example, if many droplets are quickly starting to fluoresce at low cycle numbers this may indicate that the real time mode 72 will likely be used do large numbers of copies of nucleic acid causing early fluorescence. Conversely, if many cycles occur without substantially all of the droplets 10 fluorescing, this may indicate the presence of a low copy numbers in the initial sample and thus the digital mode 70 can be used. For example, the rate of change of this ratio could be looked at as a function of cycle number to determine what mode is likely to be used. For example, if the number of positive droplets 10 rapidly increasing at early cycle numbers, this may indicate that there are a large number of copies of the target nucleic acid present and the real time mode 72 is likely to be used. Conversely, if the number of positive droplets 10 is low and not rapidly increasing, this may indicate that there are few copies of nucleic acid present and the digital mode 70 is likely to be used. To this end, one could also look at the overall fluorescence levels observed by the camera 46 and the rate of change of the same to determine modes 70, 72.

As noted above, when a low ratio or percentage of droplets 10 are positive, according to one embodiment, the system 30 operates in the digital mode 70. At higher concentrations, all or nearly all of droplets 10 will amplify and the cycle-threshold for detection will begin to shift toward an earlier cycle number. Beyond the digital regime, the real-time mode 72 is used and qPCR analysis technique can be used to determine even greater concentrations of original nucleic acid content. This would allow a dynamic range of $10^6$-$10^7$ in the digital regime, with an additional $10^5$-$10^7$ in the real-time analog regime to obtain $10^{10}$-$10^{13}$ total dynamic range PCR given the use of both the digital mode 70 and the real time mode 72. The limit of dynamic range would only be limited by the number of individual digital reactors that can be analyzed, the total volume of the combined reactors, and the maximum limit of solubility of DNA in the solution. While the invention has primarily been described in the context of using different discrete droplets 10 as reactors, the principles would also hold true nanowell or microwell based embodiments that have large numbers of discrete testing locations that operate as separate reactors.

While embodiments of the present invention have been shown and described, various modifications may be made without departing from the scope of the present invention. The invention, therefore, should not be limited, except to the following claims, and their equivalents.

What is claimed is:

1. A method of quantifying nucleic acids in a sample comprising:
   generating a plurality of aqueous phase droplets in oil within a microfluidic device, wherein at least some of the aqueous phase droplets comprise a nucleic acid, amplification reagents, and a fluorescent probe or dye contained therein;

delivering the plurality of aqueous phase droplets to a collection chamber to form an array of droplets contained therein;

thermally cycling the aqueous phase droplets within the collection chamber a plurality of times to perform nucleic acid amplification within the droplets;

imaging the array of droplets during the plurality of thermal cycles;

imaging the array of droplets at endpoints of the plurality of thermal cycles;

determining a ratio or percentage of aqueous phase droplets within the array exhibiting fluorescence from the total number of aqueous phase droplets at the thermal cycle endpoints;

outputting a first initial concentration of nucleic acid in the sample based on the ratio or percentage of aqueous phase droplets exhibiting fluorescence of the total number of aqueous phase droplets within the array at the thermal cycle endpoints; and outputting a second initial concentration of nucleic acid in the sample based on a cycle threshold (Ct) of one or more aqueous phase droplets within the array, wherein the first and second initial concentrations are outputted.

2. The method of claim 1, wherein the cycle threshold (Ct) is obtained for an individual aqueous phase droplet.

3. The method of claim 1, wherein the cycle threshold (Ct) is obtained for a plurality of aqueous phase droplets.

4. The method of claim 1, wherein the array of droplets comprise a two dimensional array of droplets.

5. The method of claim 1, wherein the array of droplets comprise a three dimensional array of droplets.

6. The method of claim 1, wherein the first and the second initial concentration of nucleic acid in the sample are calculated by software executed by one or more processors.

7. The method of claim 1, wherein the first initial concentration of nucleic acid is calculated using the formula $-\ln(1-x)$ where x is the fraction of positive aqueous phase droplets exhibiting fluorescence to the total number of aqueous phase droplets in the array.

8. The method of claim 1, further comprising outputting a final initial concentration that is calculated based on an average of the first initial concentration calculated using the ratio or percentage of aqueous phase droplets exhibiting fluorescence of the total number of aqueous phase droplets within the array and the second initial concentration of nucleic acid in the sample based on the cycle threshold (Ct) of one or more aqueous phase droplets within the array.

9. The method of claim 1, wherein the cycle threshold (Ct) is an average cycle threshold (Ct) of a plurality of aqueous phase droplets.

10. The method of claim 1, wherein imaging of the array during the plurality of thermal cycles comprises obtaining a plurality of images between the beginning and the end of each thermal cycle.

11. The method of claim 1, wherein the nucleic acid amplification comprises PCR amplification and the amplification reagents comprise PCR reagents.

* * * * *